(12) United States Patent
Benkley et al.

(10) Patent No.: US 12,025,607 B2
(45) Date of Patent: Jul. 2, 2024

(54) UTILIZING WASTE PRODUCTS BY COMPOSITIONAL ANALYSIS

(71) Applicant: Halliburton Energy Services, Inc., Houston, TX (US)

(72) Inventors: James Robert Benkley, Duncan, OK (US); Darrell Chad Brenneis, Marlow, OK (US); Thomas Jason Pisklak, Cypress, TX (US); Ronnie Glen Morgan, Waurika, OK (US)

(73) Assignee: Halliburton Energy Services, Inc., Houston, TX (US)

( * ) Notice: Subject to any disclaimer, the term of this patent is extended or adjusted under 35 U.S.C. 154(b) by 1353 days.

(21) Appl. No.: 16/479,821

(22) PCT Filed: Feb. 22, 2017

(86) PCT No.: PCT/US2017/018933
§ 371 (c)(1),
(2) Date: Jul. 22, 2019

(87) PCT Pub. No.: WO2018/156116
PCT Pub. Date: Aug. 30, 2018

(65) Prior Publication Data
US 2020/0333318 A1 Oct. 22, 2020

(51) Int. Cl.
*G01N 33/38* (2006.01)
*C04B 18/08* (2006.01)
(Continued)

(52) U.S. Cl.
CPC ............ *G01N 33/383* (2013.01); *C04B 18/08* (2013.01); *C04B 18/12* (2013.01); *C04B 18/146* (2013.01);
(Continued)

(58) Field of Classification Search
CPC .......... G01N 33/383; C04B 18/04–305; C04B 22/002; C04B 22/0026; C04B 22/0033; C04B 22/004; C04B 41/502
See application file for complete search history.

(56) References Cited

U.S. PATENT DOCUMENTS 5,106,422 A * 4/1992 Bennett .................. E01C 11/005
106/DIG. 1
5,549,859 A * 8/1996 Andersen ................ B32B 27/20
264/102
(Continued)

FOREIGN PATENT DOCUMENTS

CA 2887637 A1 * 5/2014 ............. A61P 35/00
CN 102648411 A 8/2012
(Continued)

OTHER PUBLICATIONS

Russian Office Action and Search Report for Application No. 2019123152 dated Jun. 5, 2020.
(Continued)

*Primary Examiner* — Herbert K Roberts
(74) *Attorney, Agent, or Firm* — Thomas Rooney; Tumey Law Group PLLC

(57) ABSTRACT

Methods, systems, and compositions for wellbore cementing are provided. A method may comprise: analyzing an industrial byproduct and one or more additional components to generate data about physical and/or chemical properties of the industrial byproduct; determining a concentration of the byproduct and the one or more additional components based on the data to provide a settable composition having a twenty-four destructive compressive strength at 100° F. to 200° F. of about 50 psi or greater.

18 Claims, 2 Drawing Sheets

(51) Int. Cl.

| | | |
|---|---|---|
| *C04B 18/12* | (2006.01) | |
| *C04B 18/14* | (2006.01) | |
| *C04B 18/162* | (2023.01) | |
| *C04B 28/04* | (2006.01) | |
| *C04B 28/18* | (2006.01) | |
| *C09K 8/467* | (2006.01) | |
| *G01N 15/02* | (2006.01) | |
| *G16C 60/00* | (2019.01) | |

(52) U.S. Cl.
CPC ............ *C04B 18/162* (2013.01); *C04B 28/04* (2013.01); *C04B 28/18* (2013.01); *C09K 8/467* (2013.01); *G01N 15/02* (2013.01); *G16C 60/00* (2019.02)

(56) References Cited

U.S. PATENT DOCUMENTS

| | | |
|---|---|---|
| 7,607,484 B2 | 10/2009 | Roddy et al. |
| 7,631,692 B2 | 12/2009 | Roddy et al. |
| 7,806,183 B2 | 10/2010 | Roddy et al. |
| 7,892,352 B2 | 2/2011 | Roddy et al. |
| 8,281,859 B2 | 10/2012 | Roddy et al. |
| 8,333,240 B2 | 12/2012 | Roddy et al. |
| 8,486,869 B2 | 7/2013 | Brenneis et al. |
| 8,609,592 B2 | 12/2013 | Guenthenspberger et al. |
| 8,609,595 B2 | 12/2013 | Morgan et al. |
| 8,851,173 B2 | 10/2014 | Brothers et al. |
| 8,997,578 B2 | 4/2015 | Morgan et al. |
| 9,023,150 B2 | 5/2015 | Brenneis et al. |
| 9,212,534 B2 | 12/2015 | Ballew et al. |
| 9,505,972 B2 | 11/2016 | Iverson et al. |
| 9,644,132 B2 | 5/2017 | Morgan et al. |
| 10,370,579 B2 | 8/2019 | Agapiou et al. |
| 11,174,198 B2 | 11/2021 | Morgan et al. |
| 2005/0252420 A1* | 11/2005 | Timmons ............... C04B 28/021 106/705 |
| 2010/0224365 A1 | 9/2010 | Abad |
| 2015/0024976 A1 | 1/2015 | Albrighton et al. |
| 2015/0184060 A1* | 7/2015 | Morgan ................... C09K 8/46 106/692 |
| 2015/0321953 A1 | 11/2015 | Porcherie |
| 2017/0364607 A1* | 12/2017 | Kaushik ................. C09K 8/00 |
| 2018/0037501 A1* | 2/2018 | Guynn ................... C04B 18/08 |

FOREIGN PATENT DOCUMENTS

| | | |
|---|---|---|
| CN | 104812868 A | 7/2015 |
| RU | 2021489 | 10/1994 |
| WO | 2016122531 | 8/2016 |

OTHER PUBLICATIONS

Search Report for Chinese Application No. 2017800855444 dated Feb. 2, 2021.

ISRWO International Search Report and Written Opinion for PCT/US2017/018933 dated Feb. 22, 2017.

* cited by examiner

UTILIZING WASTE PRODUCTS BY COMPOSITIONAL ANALYSIS

BACKGROUND

In well cementing, such as well construction and remedial cementing, cement compositions are commonly utilized. Cement compositions may be used in a variety of subterranean applications. For example, in subterranean well construction, a pipe string (e.g., casing, liners, expandable tubulars, etc.) may be run into a well bore and cemented in place. The process of cementing the pipe string in place is commonly referred to as "primary cementing." In a typical primary cementing method, a cement composition may be pumped into an annulus between the walls of the well bore and the exterior surface of the pipe string disposed therein. The cement composition may set in the annular space, thereby forming an annular sheath of hardened, substantially impermeable cement (i.e., a cement sheath) that may support and position the pipe string in the well bore and may bond the exterior surface of the pipe string to the subterranean formation. Among other things, the cement sheath surrounding the pipe string functions to prevent the migration of fluids in the annulus, as well as protecting the pipe string from corrosion. Cement compositions also may be used in remedial cementing methods, for example, to seal cracks or holes in pipe strings or cement sheaths, to seal highly permeable formation zones or fractures, to place a cement plug, and the like.

A particular challenge in well cementing is the development of satisfactory mechanical properties in a cement composition within a reasonable time period after placement in the subterranean formation. Previously, industrial and agricultural waste materials have been included in cement compositions to save on cost. The waste materials may not be compatible with the cement composition and may have undesired or secondary effects in addition to the primary effect of having cementitious properties. Additionally, due to factors such as insufficient reactivity of the waste materials, the amount of Portland replaced by the waste materials may be limited. Furthermore, the waste materials disclosed herein may generally be considered unsuitable for use in a cement composition due to strong negative effects the waste materials may have. Disclosed herein are methods and systems that allow the use of waste materials previously considered unsuitable for cement compositions.

BRIEF DESCRIPTION OF THE DRAWINGS

These drawings illustrate certain aspects of some of the embodiments of the present invention, and should not be used to limit or define the invention.

DETAILED DESCRIPTION

Figure 1:
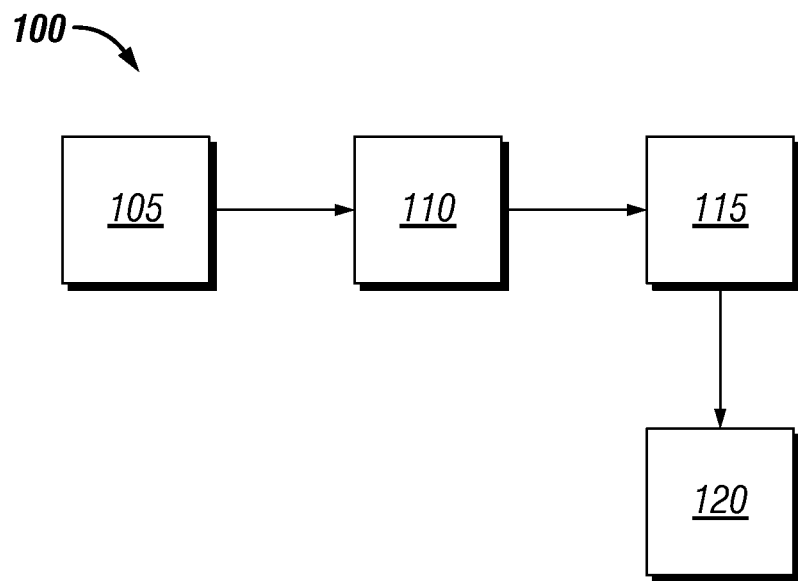
FIG. 1 is a schematic illustration of an example system for analyzing cement components.

The present disclosure may generally relate to cementing methods and systems. Provided herein are methods that may include designing a cement composition comprising waste materials that takes into account the physiochemical properties of each waste material. The method may involve analyzing a waste material generally unsuitable for wellbore cementing and balancing the waste material with other cementitious components to generate a cement composition that is suitable for use. Suitable for use as used herein means that the composition is mixable, has the desired engineering properties, and has the desired cost for a particular application. One method of improving a cement composition design may be determining a ratio of lime to silica to provide an improved ratio to affect certain cement properties. In particular, the physiochemical properties may include the composition of each waste material. The composition of the waste materials may affect the final set mechanical properties of the cement composition as well as the dynamic or time based properties such as mixability, rheology, viscosity, and others. Every waste material may affect one or more of the properties mentioned. As previously mentioned, waste materials as described herein refer to materials that may be generally unsuitable for use in a cement. Waste materials may be industrial byproducts. As used herein, the term "industrial byproduct" refers to a secondary product derived from a manufacturing process. In other words, the industrial byproduct is not the primary product being produced from the manufacturing process. For example, a fly ash from a certain coal plant may comprise a relatively large amount of free lime. If used in a cement composition the large amount of free lime may negatively interact with the other components in the cement composition leading to poor performance. The techniques described herein may allow one of ordinary skill in the art to analyze waste products unsuitable for use in a cement and through a cement composition design process, may enable the waste material to still be utilized. The techniques described herein may allow one of ordinary skill to develop cement compositions with materials that may have previously been discarded.

In previous Portland cement based cement composition designs, a waste material may be added as a filler to reduce cost without taking into account the composition or reactivity of the materials. A waste material (e.g., slag) may be too reactive or unbalanced in a particular mineral when compared to other waste materials used in cement. In some examples, the waste material may be so unbalanced that the waste material is unsuitable for use in cementing due to the large negative effects the waste material has. A material may, for example, comprise a large amount of free lime which may lead to poor setting when combined with a Portland cement. In previous cement compositions, waste materials with a large negative effect may not have been considered suitable for use and subsequently discarded or not used. Typically, the waste material may be tested in several cement compositions or formulations to determine if the waste material may be suitable. A waste material from a particular region may be compositionally different than the same type waste material of another region. Compositional differences in the waste materials may make one more suitable than the other or make one entirely unsuitable. One method to determine how the waste material will perform is though standard cement set tests defined by the American Petroleum Institute (API). A cement set test and other tests may be performed on a cement composition comprising the waste material and based on the results an engineer may determine if the waste material should be used in a cement composition. If the waste material does not pass the tests, it may not ever be used or considered.

The techniques described herein may allow one of ordinary skill to analyze a waste material and determine a priori whether a waste material will be suitable for use and if any modifications or turning are needed to reduce any negative effects the waste material may have. The techniques described herein may also allow the use of waste materials that would not normally be suitable for cement use. The cement composition design process disclosed herein may comprise tuning the waste material in order to increase the overall mechanical properties of the composition. Another cement composition design process disclosed herein may minimize cost by utilizing multiple waste materials or cement components and balancing the reactivity of each. Reactivity of the waste material may be controlled or tuned by adjusting relative amounts of minerals present. Minerals may include but are not limited to lime, silica or silicic acid, gypsum, metal hydrates, metal oxides such as alumina, and others. A cement composition as disclosed herein may be generally categorized as a synthetic Portland cement composition. Although the cement composition disclosed herein may not match the oxide concentration of a Portland cement, the cement composition may meet or exceed the mechanical properties of a cement composition based on Portland cement. Additionally, the cement components, such as waste materials, disclosed herein may generally be described as alkali soluble. A cement component is considered alkali soluble where it is at least partially soluble in an aqueous solution of pH 7.0 or greater.

The cement compositions generally may comprise water, Portland cement, a waste material, and lime. The cement compositions may have a density suitable for a particular application. The cement compositions may comprise any suitable density, including, but not limited to, a density in the range of about 8 pounds per gallon ("ppg") to about 16 ppg (1 g/cm$^3$ to 1.9 g/cm$^3$). In foamed examples, the foamed cement compositions of the present invention may have a density in the range of about 8 ppg to about 13 ppg (1 g/cm$^3$ to 1.6 g/cm$^3$) (or even lower). The cement compositions comprise other means to reduce their densities, such as hollow microspheres, low-density elastic beads, or other density-reducing additives known in the art. Those of ordinary skill in the art, with the benefit of this disclosure, should recognize the appropriate density for a particular application.

The water used in the cement compositions may include, for example, freshwater, saltwater (e.g., water containing one or more salts dissolved therein), brine (e.g., saturated saltwater produced from subterranean formations), seawater, or combinations thereof. Generally, the water may be from any source, provided that it does not contain an excess of compounds that may undesirably affect other components in the cement composition. The water may be included in an amount sufficient to form a pumpable slurry. The water may be included in the cement compositions in any suitable amount, including, but not limited to, about 40% to about 200% by weight of cementitious components ("bwoc") present in the cement composition. As used herein, the term "cementitious component" refers to materials that possess cementitious properties, such as materials with hydraulic, pozzolanic, or other cementitious activity including Portland cement and the waste materials, among others. For the purposes of this disclosure, lime is also considered a cementitious component as it may react with various oxides in the pozzolanic and other cementitious reactions. In some examples, the water may be included in an amount in the range of about 40% to about 150% bwoc. Those of ordinary skill in the art, with the benefit of this disclosure, should be able to select an appropriate amount and type of water for a particular application.

Portland cements that are suited for use in the present disclosure may be classified as Classes A, C, G, and H cements according to American Petroleum Institute, API Specification for Materials and Testing for Well Cements, API Specification 10, Fifth Ed., Jul. 1, 1990. In addition, in some examples, cements suitable for use in the present invention may be classified as ASTM Type I, II, or III. Cement compositions that may be considered "low Portland" may be designed by use of the techniques disclosed herein in that the cement compositions may comprise Portland cement in an amount of about 50% or less by weight of cementitious components ("bwoc"). In addition to Portland cements, other hydraulic cements including, but not limited to, those comprising calcium, aluminum, silicon, oxygen, iron, and/or sulfur, which set and harden by reaction with water. Suitable hydraulic cements may include gypsum, and high alumina content cements, among others present in the composite cement composition. The Portland cement may be present in the cement compositions in any suitable amount, including, but not limited to, an amount in the range of about 0% to about 50% bwoc. In some examples the Portland cement may be present in an amount ranging between any of and/or including any of about 1%, about 5%, about 10%, about 20%, about 40%, or about 50% bwoc. Cement compositions may also be designed that are free (or essentially free) of Portland cement. Those of ordinary skill in the art, with the benefit of this disclosure, should be able to select an appropriate amount of hydraulic cement for a particular application.

The cement compositions may comprise a waste material. As used herein, the term "waste material" refers to a material that an industry would normally dispose of because it cannot be sold or used otherwise. Examples of suitable waste materials may include, but are not limited to, fly ash, drill cuttings, cement kiln dust ("CKD"), silica fume, bio-ashes, and other waste pozzolans, among others. Bio-ashes may generally be the product of intentional combustion of agricultural, municipal, and industrial organic wastes. Bio-ashes may include, but are not limited to, agricultural waste ash, such as rice husk ash, sugar cane ash, and bagasse ash. Furthermore, in certain examples of the cement compositions disclosed herein, the waste material may comprise a mixture of one or more waste materials. In general, the waste materials comprise various oxides such as, for example, $CaCO_3$, $SiO_2$, CaO, $K_2SO_4$, $CaSO_4$, $Al_2O_3$, and $Fe_2O_3$, MgO, $SO_3$, $Na_2O$, $K_2O$, $TiO_2$, among many others. Some oxides may dissolve or otherwise dissociate to provide, among other things, silicic acid that can react to form a cement product. By inclusion of the waste material, a different path may be used to arrive at a similar product as from Portland cement. A pozzolanic reaction may be induced wherein silicic acid ($H_4SiO_4$) and portlandite (Ca(OH)$_2$) react to form a cement product (calcium silicate hydrate). If other compounds, such as, aluminate, are present in the silica source, additional reactions may occur to form additional cement products, such as calcium aluminate hydrates. Calcium hydroxide necessary for the reactions may be provided from other cement components, such as Portland cement and potentially from one or more waste materials, or may be separately added to the cement composition.

An example of a suitable waste material may comprise fly ash. A variety of fly ashes may be suitable, including fly ash classified as Class C and Class F fly ash according to American Petroleum Institute, API Specification for Materials and Testing for Well Cements, API Specification 10, Fifth Ed., Jul. 1, 1990. Class C fly ash comprises both silica and lime, so it may set to form a hardened mass upon mixing with water. Class F fly ash generally does not contain a sufficient amount of lime to induce a cementitious reaction, therefore, an additional source of calcium ions may be necessary for a composite cement composition comprising Class F fly ash. In some embodiments, lime may be mixed with Class F fly ash in an amount in the range of about 0.1% to about 100% by weight of the fly ash. In some instances, the lime may be hydrated lime. Suitable examples of fly ash comprise, but are not limited to, POZMIX® A cement additive, commercially available from Halliburton Energy Services, Inc., Houston, Texas.

Another example of a suitable waste material may comprise slag. Slag is generally a by-product in the production of various metals from their corresponding ores. By way of example, the production of cast iron may produce slag as a granulated, blast furnace by-product with the slag generally comprising the oxidized impurities found in iron ore. Slag generally does not contain sufficient basic material, so slag may be used with a base to produce a settable composition that may react with water to set to form a hardened mass. Examples of suitable sources of bases include, but are not limited to, sodium hydroxide, sodium bicarbonate, sodium carbonate, lime, and combinations thereof.

Another example of a suitable waste material may comprise silica fume. Silica fume may alternatively be referred to as "microsilica" or "condensed silica fume." Silica fume is generally a byproduct material that may be obtained, for example, by reduction of quartz with coal in the manufacture of certain alloys. Silica fume may be processed after recovery, for example, to control particle size. Silica fume may be extremely fine, for example, with a mean particle size of less than 1 micron and, alternatively, less than 0.2 microns. The mean particle size, as used herein, corresponds to d50 values as measured by particle size analyzers such as those manufactured by Malvern Instruments, Worcestershire, United Kingdom. Silica fume may have a high surface area and is generally available in either a powder form or liquid.

Another example of a suitable waste material may comprise CKD. Cement kiln dust or "CKD", as that term is used herein, refers to a partially calcined kiln feed which is removed from the gas stream and collected, for example, in a dust collector during the manufacture of cement. Usually, large quantities of CKD are collected in the production of cement that are commonly disposed of as waste. Disposal of the CKD as waste can add undesirable costs to the manufacture of the cement, as well as the environmental concerns associated with its disposal.

Another example of a suitable waste material may comprise an agricultural waste ash. Examples of agricultural waste ash that may be used in the composite cement composition comprise, for example, wood (e.g., sawdust, bark, twigs, branches, other waste wood) ash, tree leave ash, corn cob ash, rice hull ash, cane (e.g., sugar cane) ash, bagasse ash, grain (e.g., amaranth, barley, corn flaxseed, millet, oat, quinoa, rye, rice, wheat etc.) and related by-product(s) (e.g., husks, hulls, etc.) ash, orchard ash, vine trimming ash, grass (e.g., Korai, Tifton, native shiba, etc.) ash, straw ash, groundnut shell ash, legume (e.g., soybean) ash, and combinations thereof.

The waste material may be present in the cement compositions in any amount suitable for a particular application, including, but not limited to, an amount in the range of about 10% to about 100% bwoc, from about 50% to about 100% bwoc, from about 50% to about 80% bwoc, or from 80% about 100% bwoc. In some examples the waste material may be present in an amount ranging between any of and/or including any of about 1%, about 5%, about 10%, about 20%, about 40%, about 60%, about 80%, or about 90% bwoc. Those of ordinary skill in the art, with the benefit of this disclosure, should be able to select an appropriate type and amount of waste material for a particular application.

The cement compositions may comprise lime. Lime may be present in the cement composition in different forms, including as calcium oxide and/or calcium hydroxide. As used herein, the term "lime" is intended to include both calcium oxide and calcium hydroxide. Calcium hydroxide is also commonly referred to as hydrated lime and slaked lime. In some examples, the hydrated lime may be provided as quicklime (calcium oxide) which hydrates when mixed with water to form the hydrated lime. In addition the addition of lime as a separate component, at least a portion of the lime in cement composition may be also provided from other cement components. For example, the hydraulic reaction of Portland cement with water may release hydrated lime into the cement composition. In addition, the waste materials may also contain lime or release lime into the cement composition. Lime present in a waste material as CaO may be referred to as free lime if it is not bound to other minerals. The hydrated lime may be included in examples of the cement compositions, for example, to react with the waste materials. Where present, the lime may be included in the cement compositions in an amount in the range of from about 10% to about 100% bwoc, for example. In some examples, the hydrated lime may be present in an amount ranging between any of and/or including any of about 10%, about 20%, about 40%, about 60%, about 80%, or about 100% bwoc. One of ordinary skill in the art, with the benefit of this disclosure, should recognize the appropriate amount of hydrated lime to include for a chosen application.

In some examples, the cement compositions may comprise a calcium source in place of, or in addition to, hydrated lime. In general, calcium and a high pH, for example a pH of 7.0 or greater, may be needed for certain cementitious reactions to occur. A potential advantage of hydrated lime may be that calcium ions and hydroxide ions are supplied in the same molecule. In another example, the calcium source may be $Ca(NO_3)_2$ or $CaCl_2$ with the hydroxide being supplied form NaOH or KOH, for example. One of ordinary skill would understand the alternate calcium source and hydroxide source may be included in a cement composition in the same way as hydrated lime. For example, the calcium source and hydroxide source may be included in a silica source-to-hydrated-lime weight ratio of about 10:1 to about 1:1 or a ratio of about 3:1 to about 5:1. Where present, the alternate calcium source and hydroxide source may be included in the cement compositions in an amount in the range of from about 10% to about 100% by weight of the silica source, for example. In some examples, the alternate calcium source and hydroxide source may be present in an amount ranging between any of and/or including any of about 10%, about 20%, about 40%, about 60%, about 80%, or about 100% by weight of the silica source. One of ordinary skill in the art, with the benefit of this disclosure, should recognize the appropriate amount of alternate calcium source and hydroxide source to include for a chosen application.

The cement composition may further comprise other additives suitable for use in cementing operations. Examples of such additives include, but are not limited to: weighting agents, retarders, accelerators, activators, gas control additives, lightweight additives, gas-generating additives, mechanical-property-enhancing additives, lost-circulation materials, filtration-control additives, fluid-loss-control additives, defoaming agents, defoaming agents, foaming agents, transition time modifiers, dispersants, thixotropic additives, suspending agents, and combinations thereof. One of ordinary skill in the art, with the benefit of this disclosure, should be able to select an appropriate additive for a particular application.

The cement compositions may be prepared using any suitable technique. The cementitious components, such as the Portland cement, waste materials, and/or lime may be dry blended prior to combination with the water to form the cement composition. This dry blend may be prepared offsite and then transported to the well site, for example, where it may be combined with the water. Additional solid cement additive may also be included in the dry blend. Other suitable techniques may be used for preparation of the cement compositions as should be appreciated by those of ordinary skill in the art in accordance with the present disclosure.

As previously described, the waste material may dissolve or otherwise form silicic acid that can react with calcium hydroxide to form a cement product. Additionally, other oxides and compounds present in the waste materials may also dissolve and react with lime and other cementitious components to form a hardened mass. A pozzolanic reaction may be induced wherein silicic acid ($H_4SiO_4$) and portlandite ($Ca(OH)_2$) react to form a cement product (calcium silicate hydrate). This pozzolanic reaction between silicic acid ($H_4SiO_4$) and portlandite ($Ca(OH)_2$) may progress according to the following equations. First, silica may be hydrated to form silicic acid and calcium oxide may be hydrated to form portlandite or hydrated lime. As will be appreciated by those of ordinary skill in the art, calcium hydroxide may also be provided from other components in the cement composition, for example, by hydraulic reaction of Portland cement. Next, silicic acid and hydrated lime may react to form calcium silicate hydrate. If other compounds, such as, aluminate, are present in the silica source, additional reactions may occur to form additional cementitious products, such as calcium aluminate hydrates.

$$SiO_2 + 2H_2O \rightarrow H_4SiO_4$$

$$CaO + H_2O \rightarrow Ca(OH)_2$$

$$H_4SiO_4 + Ca(OH)_2 \rightarrow CaO_{1.7} \cdot SiO_2 \cdot xH_2O$$

The reaction may not be straightforward as the different waste materials may have different solubility and hydration rates. The stoichiometry of the reaction may also not straight forward due to the differing solubility of the reactants. If the amount of either reactant is different than an ideal amount, then the reaction may slow or stop. One way to control the reaction may be to provide a ratio of available lime and silicic acid that is sufficient to drive the reaction. In other words, concentrations of silica sources and/or lime may be selected for the cement composition to provide this ratio.

A cement composition may be designed to have a target lime-to-silica ratio. Any suitable target lime-to-silica ratio may be selected to provide the desired reaction, including, but not limited to, a target lime-to-silica ratio ranging from about 20/80 lime to silica by weight to about 40/60 lime to silica by weight, for example, be about 20/80 lime to silica by weight, about 30/70 silica to lime by weight, or about 40/60 lime to silica by weight.

The waste materials suitable for use in a cement compound may vary widely in composition depending on the specific source and region where the waste material was produced. In previous cement compositions comprising waste materials, the specific chemical makeup of the waste material was often not taken into account. Some of the waste products may be chemically imbalanced where they may cause severe issues such as gelation, high heat generation, mineral incompatibility, and other undesired effects. Previously, these materials may have been deemed unsuitable for use in cement due to the large negative effects. In some examples, a waste material may be relatively high in free lime which if used on its own with Portland cement may cause the cement composition to not attain the desired compressive strength. The high lime content and low silica content of a specific waste material may cause undesired reactions, especially in low Portland cement compositions.

The waste materials (one or more additional components, such as cementitious components, including source of silica and/or lime) may be tested for physical and chemical properties using laboratory techniques and procedures including, but not limited to, microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio. One or more of the preceding tests may be consider API tests, as set forth in the API recommended practice for testing well cements (published as ANSI/API recommended practice 10B-2). Additional API tests not specifically listed above may also be used for the measurements. The physical and chemical properties may be measured for a group of cement components. Two or more of the cement components measured may be different types of cement components (e.g., volcanic rock, CKD, fly ash, etc.). Two or more of the cement components may be the same type but from different sources (e.g., volcanic rock from source 1, volcanic rock from source 2, etc.).

X-ray powder diffraction is one analysis technique that may be used for measuring the physical and chemical properties of the waste materials. X-ray powder diffraction is a technique of exposing a sample to x-rays, neutrons, or electrons and measuring the amount of inter-atomic-diffraction. The sample acts a diffraction grating thereby producing a differing signal at different angles. The typical properties that may be measured are the phase identification for the identification and characterization of a crystalline solid. Other properties may be crystallinity, lattice parameters, expansion tensors, bulk modulus, and phase transitions.

X-ray fluorescence is another analysis technique that may be used for measuring the physical and chemical properties of the waste materials. X-ray fluorescence may use short wave x-rays to ionize atoms in a sample thereby causing them to fluoresce at certain characteristic wavelengths. The characteristic radiation released by a sample may allow accurate identification of the component atoms in the sample as well as their relative amounts.

Particle size analysis is another analysis technique that may be used for measuring the physical and chemical properties of the waste materials (and/or one or more additional components) may. Particle size analysis may be accomplished through analysis by various laboratory techniques including but not limited to laser diffraction, dynamic light scattering, static image analysis, and dynamic image analysis. Particle size analysis may also provide information about the morphology of a particular sample. Morphology may include parameters such as sphericity and roundness as well as the general shape of a particle such as disk, spheroid, blade, or roller. With a knowledge of the morphology and particle size, the average surface area and volume may be estimated. Surface area and volume may be important in determining the water requirement as well as reactivity. In general, a relatively smaller particle size may react more quickly than a relatively larger particle size. Also the relatively smaller particle size may have a greater water requirement to completely hydrate than a relatively larger particle size.

Energy dispersive x-ray spectroscopy is another analysis technique that may be used for measuring the physical and chemical properties of the waste materials (and/or one or more additional components) may. Energy dispersive x-ray spectroscopy is an analytical technique used to analyze the elements present in a sample and determine the chemical characterization of a sample. Other techniques may include Fourier transform infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma mass spectrometry (ICP-MS), thermal ionization mass spectroscopy, glow discharge mass spectroscopy, and x-ray photoelectron spectroscopy.

The waste materials (and/or one or more additional components) may be analyzed to determine their water requirement. Water requirement is typically defined as the amount of mixing water that is required to be added to a powdered, solid material to form a slurry of a specified consistency. Water requirement for a particular cement component may be determined by a process that includes a) preparing a Waring blender with a specified amount of water, b) agitating the water at a specified blender rpm, c) adding the powdered solid that is being investigated to the water until a specified consistency is obtained, and d) calculating the water requirement based on the ratio of water to solids required to reach the desired consistency.

The waste materials (and/or one or more additional components) may be analyzed to determine their specific surface area. Specific surface area generally refers to the total surface area and may be reported as the total surface area per unit mass. Values obtained for specific area are dependent on the analysis technique. Any suitable analysis technique may be used, including, but not limited to, adsorption based methods such as Brunauer-Emmett-Teller (BET) analysis, methylene blue staining, ethylene glycol monoethyl ether adsorption, and a protein-retention method, among other.

Thermogravimetric analysis is another analysis technique that may be used for measuring the physical and chemical properties of the waste materials (and/or one or more additional components) may. Thermogravimetric analysis is a method of thermal analysis wherein changes in physical and chemical properties of a sample may be measured. In general the properties may be measured as a function of increasing temperature, such as with a constant heating rate, or as a function of time with a constant temperature or a constant mass change. Properties determined by thermogravimetric analysis may include first-order phase transitions and second-order phase transitions such as vaporization, sublimation, adsorption, desorption, absorption, chemisorption, desolvation, dehydration, decomposition, oxidation and reduction reactions, ferromagnetic transition, superconducting transition, and others.

In addition to determining physical and chemical properties of the waste materials themselves (and/or one or more additional components) may, laboratory tests may also be run to determine behavior of the waste materials in a cement composition. For example, the cement components may be analyzed in a cement composition to determine their compressive strength development and mechanical properties. For example, a preselected amount of the cement component may be combined with water and lime (if needed for setting). The mechanical properties of the cement composition may then be determined including, compressive strength, tensile strength, and Young's modulus. Any of a variety of different conditions may be used for the testing so long as the conditions are consistent for the different cement components.

Compressive strength is generally the capacity of a material or structure to withstand axially directed pushing forces. The compressive strength of the cement component may be measured at a specified time after the cement component has been mixed with water and the resultant cement composition is maintained under specified temperature and pressure conditions. For example, compressive strength can be measured at a time in the range of about 24 to about 48 hours (or longer) after the fluid is mixed and the fluid is maintained at a temperature of from 100° F. to about 200° F. and atmospheric pressure. Compressive strength can be measured by either a destructive method or non-destructive method. The destructive method physically tests the strength of treatment fluid samples at various points in time by crushing the samples in a compression-testing machine. The compressive strength is calculated from the failure load divided by the cross-sectional area resisting the load and is reported in units of pound-force per square inch (psi). Non-destructive methods typically may employ an Ultrasonic Cement Analyzer ("UCA"), available from Fann® Instrument Company, Houston, TX Compressive strengths may be determined in accordance with API RP 10B-2, *Recommended Practice for Testing Well Cements*, First Edition, July 2005.

Tensile strength is generally the capacity of a material to withstand loads tending to elongate, as opposed to compressive strength. The tensile strength of the cement component may be measured at a specified time after the cement component has been mixed with water and the resultant cement composition is maintained under specified temperature and pressure conditions. For example, tensile strength can be measured at a time in the range of about 24 to about 48 hours (or longer) after the fluid is mixed and the fluid is maintained at a temperature of from 100° F. to about 200° F. and atmospheric pressure. Tensile strength may be measured using any suitable method, including those in accordance with the procedure described in ASTM 0307. That is, specimens may be prepared in briquette molds having the appearance of dog biscuits with a one square inch cross-sectional area at the middle. Tension may then be applied at the enlarged ends of the specimens until the specimens break at the center area. The tension in pounds per square inch at which the specimen breaks is the tensile strength of the material tested.

Young's modulus also referred to as the modulus of elasticity is a measure of the relationship of an applied stress to the resultant strain. In general, a highly deformable (plastic) material will exhibit a lower modulus when the confined stress is increased. Thus, the Young's modulus is an elastic constant that demonstrates the ability of the tested material to withstand applied loads. A number of different laboratory techniques may be used to measure the Young's modulus of a treatment fluid comprising a cementitious component after the treatment fluid has been allowed to set for a period of time at specified temperature and pressure conditions.

Although only some select laboratory techniques may have been mentioned, it should be understood that there may many analytical techniques that may be appropriate or not appropriate for a certain sample. One of ordinary skill in the art with the benefit of this disclosure should be able to select an appropriate analytical technique to determine a certain property of interest.

Once the analytical techniques have been performed on the waste materials (and/or one or more additional components) may, the data may be categorized and correlated. Some categories may include, but are not limited to, specific surface area, morphology, specific gravity, water requirement, etc. In some examples, the components may be categorized by the oxide composition including, but not limited to, silica content, calcium oxide content, and alumina content. In addition, correlations between the waste materials may be generated based on the categorization of the data. For example, the various categories of properties may be plotted against one another. In some examples, water requirement versus specific surface area may be plotted. Accordingly, the water requirement of the cement component may be correlated to the specific surface area so that the specific surface area is a function of water requirement. Specific surface area may be used to predict reactivity of a cement component (or components). However, specific surface area may not always be available for each material as specific surface area analysis typically requires a specialized instrument. Accordingly, if the water requirement may be obtained for the waste materials, the correlation between water requirement and specific surface area may be used to obtain an estimate for specific surface area, which may then be used to predict reactivity. In addition to correlations between specific surface area and reactivity, correlations may also be made between specific surface area and other mechanical properties such as tensile strength and Young's modulus.

In some examples the waste materials (and/or one or more additional components) may that are alkali soluble may have synergistic effects with a Portland cement while others may be incompatible. In some examples a waste material that is alkali soluble may cause gelation, high heat generation, water retention, among other effects. These and other effects may be realized during laboratory testing of the waste material. Laboratory equipment may be configured to detect the effects of the waste materials on the composition. In some examples, equipment such a calorimeter may measure and quantify the amount of heat generation per unit mass of the waste materials. Viscometers may measure the increase in gelation caused by the waste materials. Each of the physical effects caused by the addition of the waste materials may be measured at several concentrations and then categorized, e.g., plotted or mapped. Once a component is mapped, the effect of adding the waste materials to a cement composition may be predicted by referencing the categorization.

One potential advantage of analyzing the composition of the waste materials (and/or one or more additional components) may be that certain properties of the waste material may be realized. For example, using the data and/or correlations concentrations of the waste material and one or more additional components may be selected to provide a cement composition with desirable properties, such as compressive strength. By way of example, the concentrations of the water material and the one or more additional components may be selected based on the data to provide a cement composition with a twenty-four destructive compressive strength of at least about 25 psi. In some examples, a waste material may comprise a relatively high amount of a certain mineral not normally present in such a waste material or it may be realized that the waste material comprises an unexpectedly large amount of a material that is normally present in the waste material. For example, it may be realized that a certain fly ash comprises a relatively high amount of gypsum. If the same fly ash were used as a pozzolan without the knowledge of the relatively high amount of gypsum, the resulting cement composition may have poor engineering properties. In contrast, with the knowledge that the fly ash comprises a relatively high amount of gypsum, one of ordinary skill would realize that the fly ash may supplement or replace gypsum in a gypsum based cement composition. By analyzing the compositional makeup of waste materials, new uses for the materials may be realized.

A method to design a cement composition that accounts for the chemical composition of a waste material is described herein. A selected waste material may be tested using standard laboratory analysis such as, for example, x-ray fluorescence spectroscopy or another suitable technique as previously described. The laboratory testing may produce data about the compositional makeup, including oxides, present in each waste material. Once the laboratory analysis has been performed, the data may be categorized, including categorizing the waste materials by oxide composition, including, without limitation, silica content, lime content (e.g., calcium oxide), alumina content and other oxide content. The categorization may generally comprise listing in a table the silica content, calcium oxide content, and alumina content for each tested cementitious component, including the Portland cement, waste material, and/or hydrated lime. Additionally, the rate of dissolution of each component may be categorized. The rate of dissolution may be tested by other laboratory techniques known in the art.

Designing the cement composition may comprise any of a number of different steps. A waste material may be analyzed using one or more of the techniques previously discussed. Based on the compositional analysis of the waste material, the other components needed to create a suitable cement composition may be selected. Two or more cementitious components and their concentrations may be selected for an initial cement composition. In some examples, one of the cementitious components may comprise Portland cement. The lime-to-silica ratio of the two or more cementitious components may calculated. The lime-to-silica ratio may be determined using any suitable technique. Calculating the lime-to-silica ratio may include, determining a total amount of silica and a total amount of lime in the two or more cementitious components and then taking the ratio of the lime to the silica. For the purposes of the lime-to-silica ratio, the lime may be considered to be either calcium oxide or calcium hydroxide. For example, the lime-to-silica ratio may be determined by measuring the available silica and lime for a given cementitious component using standard laboratory techniques as previously described. If the calculated lime-to-silica ratio cement composition does not meet (or exceed) the target lime-to-silica ratio, the concentration of one or more cementitious components may be adjusted until the target lime-to-silica ratio may be met or exceeded. A concentration of lime (as a separate cementitious component) in the cement composition may be adjusted if there is insufficient lime. To determine how much lime to add, the net amount of silica and lime contribution from each cement component may be determined using the laboratory techniques previously described. The ratio of silica to lime may then be determined and more lime may be added until the desired ratio is achieved. If there is insufficient silica, the silica source may be adjusted until the target ratio is achieved. If other oxides are present in the cementitious components, a lime-to-oxide ratio may also be calculated. The lime-to-oxide ratio may also be adjusted in the same manner as the lime-to-silica ratio as described above until a target lime-to-oxide ratio is met or exceeded.

One potential advantage of utilizing waste materials and balancing the lime-to-silica ratio may be that the total amount of Portland cement required to meet or exceed the engineering requirements may be relatively low and potentially undesirable effects associated with the waste materials may be minimized. Generally, a cement engineer or operator may determine the required engineering properties of a cement composition for a particular well. The waste materials available in the particular region where the cement composition is to be pumped may have different levels of oxides. The available waste materials may be cataloged and laboratory testing run on each of the materials. The laboratory testing may include, without limitation, content of at least one following: silica, alumina, iron, iron, calcium, calcium, sodium, potassium, magnesium, sulfur, oxides thereof, and combinations thereof. The cement engineer may start with a cement composition of, for example, 30% by weight Portland cement with the balance weight percent being various waste materials previously tested. A target lime-to-silica ratio of be 20/80 may be selected. By using the weight percent of each component and the laboratory testing that was previously done, the lime-to-silica ratio of the cement composition may be determined. If the lime or silica is off, either may be adjusted by adding lime or more silica (e.g., by adding more silica source in the form of waste material). Once the silica-lime balance is completed the cement composition may be tested for mechanical or engineering properties. Several cement compositions may be made with varying levels of Portland cement. For example, a cement composition may comprise about 10% to about 30% Portland cement. In some examples, a cement composition may comprise about 10%, about 15%, about 20%, about 25%, or about 30% Portland cement by weight. One or ordinary skill, with the benefit of this disclosure, should be able to select a Portland cement weight percent, perform oxide analysis, determine the target lime-to-silica ratio, and adjust the weight percent of each component to create a slurry with the required engineering properties.

Any of the exemplary cement compositions disclosed herein may be introduced into a subterranean formation and allowed to set. As used herein, introducing the cement composition into a subterranean formation includes introduction into any portion of the subterranean formation, into near wellbore region surrounding the wellbore, or into both. In primary cementing applications, for example, the cement compositions may be introduced into the annular space between a conduit located in a wellbore and the walls of the wellbore (and/or a larger conduit in the wellbore), wherein the wellbore penetrates the subterranean formation. The cement composition may be prepared and allowed to set in the annular space to form an annular sheath of hardened cement. The cement composition may form a barrier that prevents the migration of fluids in the wellbore. The cement composition may also, for example, support the conduit in the wellbore. In remedial cementing applications, the cement compositions may be used, for example, in squeeze cementing operations or in the placement of cement plugs. By way of example, the cement compositions may be placed in a wellbore to plug an opening (e.g., a void or crack) in the formation, in a gravel pack, in the conduit, in the cement sheath, and/or between the cement sheath and the conduit (e.g., a microannulus).

Accordingly, this disclosure describes systems, compositions, and methods relating to slurry design process. Without limitation, the systems, compositions and methods may further be characterized by one or more of the following statements:

Statement 1. A method comprising: analyzing an industrial byproduct and one or more additional components to generate data about physical and/or chemical properties of the industrial byproduct; and determining a concentration of the byproduct and the one or more additional components based on the data to provide a settable composition having a twenty-four destructive compressive strength at 100° F. to 200° F. of about 50 psi or greater.

Statement 2. The method of statement 1 wherein the industrial byproduct comprises at least one material selected from the group consisting of fly ash, drill cuttings, cement kiln dust, silica fume, a bio-ash, and combinations thereof.

Statement 3. The method of statement 1 or statement 2 wherein the analyzing the industrial byproduct comprises analysis by one or more techniques selected from the group consisting of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio, API testing, and combinations thereof.

Statement 4. The method of any previous statement wherein the data comprises an amount of at least component selected from the group consisting of silica, alumina, iron, calcium, sodium, potassium, magnesium, sulfur, oxides thereof, and combinations thereof.

Statement 5. The method of any previous statement wherein the data comprises average particle size, particle size distribution, and morphology.

Statement 6. The method of any previous statement wherein the data comprises specific surface area.

Statement 7. The method of any previous statement further comprising determining correlations of specific surface to water requirement of the industrial byproduct.

Statement 8. The method of any previous statement wherein the one or more additional components comprise a silica source and/or lime.

Statement 9. The method of any previous statement further comprising preparing a cement composition comprising the industrial byproduct and the one or more additional cement components, introducing the cement composition into a subterranean formation, and allowing the cement composition to set.

Statement 10. The method of statement 9 wherein the cement composition is introduced into the subterranean formation using one or more pumps.

Statement 11. The method of statement 9 or statement 10 wherein the preparing a cement composition comprises mixing components of the cement composition using mixing equipment, the components comprising water, the industrial byproduct, and the one or more additional cement components.

Statement 12. The method of any previous statement wherein the cement component further comprises Portland cement.

Statement 13. The method of any previous statement further comprising preparing a sample cement composition comprising the cement additive, testing the sample cement composition to determine one or more performance characteristics selected from the group consisting of compressive strength, thickening time, and fluid loss, and adjusting concentration of one or more additives in the sample cement composition.

Statement 14. A system for analyzing industrial byproduct comprising: a plurality of industrial byproducts; an analytical instrument configured to gather data about the industrial byproducts; a computer system configured to accept the data, and generate correlations for the industrial byproducts based on the data.

Statement 15. The system of statement 14 wherein the industrial byproducts comprise at least one material selected from the group consisting of fly ash, drill cuttings, cement kiln dust, silica fume, a bio-ash, and combinations thereof, and wherein the cement component further comprises an additional silica source that is alkali soluble.

Statement 16. The system of statement 14 or statement 15 wherein the analytical instrument is configured to perform one or more of the functions selected from the group consisting group consisting of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio, API testing, and combinations thereof.

Statement 17. The system of any one of statements 14 to 16 wherein the computer system further comprises an algorithm configured to: analyze the physical and chemical data and output a predictive model; and store the predictive model in a predictive model database.

Statement 18. The system of statement 17 wherein the predictive model comprises a correlation of a specific surface area and water requirement of an industrial byproduct.

Statement 19. A system for generating cement compositions comprising: a predictive model database comprising predictive model data, reactivity maps, and raw data; a materials database, wherein the materials database comprise a silica source that is an industrial byproduct; a computer system configured to query the databases and accept input from a user; and an algorithm capable of generating calculated cement compositions.

Statement 20. The system of statement 19 wherein the algorithm is configured to generate the calculated cement compositions with a selected industrial byproduct defined by the user, wherein the selected industrial byproduct is the silica source in the materials database.

Examples of the methods of using the silica-lime balancing technique with waste materials will now be described in more detail with reference to FIG. 1. A system 100 for analyzing the cementitious components is illustrated. The system 100 may comprise a cementitious component sample 105, analytical instrument 110, and computer system 115. Cementitious component sample 105 may be any cementitious component (e.g., Portland cement, waste material, lime, etc.) of interest. The cementitious component sample may be placed or fed into analytical instrument 110. In some examples, analytical instrument 110 may be configured to automatically feed cementitious component sample 105 into analytical instrument 110. Analytical instrument 110 may be configured to analyze the physical and chemical properties of cementitious component sample 105. As previously described, physical and chemical properties may comprise, data derived oxide analysis and others tests. The data generated by analytical instrument 110 may be sent to computer system 115 for processing. Computer system 115 may comprise a processor, memory, internal storage, input and output means, network connectivity means, and/or other components common to computer systems. Computer system 115 may take the data from analytical instrument 110 as input and store it in the storage for later processing. Processing the data may comprise inputting the data into algorithms which compute a result. The computer system may be configured to analyze the oxide data from a sample and generate correlations, charts, and models related to solubility, time of dissolution, time dependent availability of oxides in solution, predicted reactivity, lime requirement, and others. The generated data and data generated from analytical instrument 110 may be stored in database 120. Database 120 may also comprise data about the cost of each cementitious component. Database 120 may be stored locally or on a network.

Figure 2:
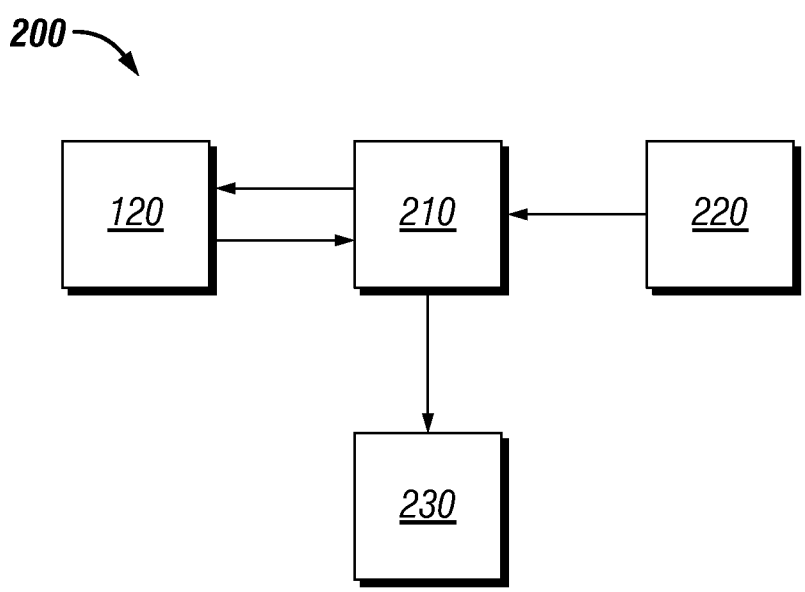
FIG. 2 is a schematic illustration of an example system for generating cement compositions.

Referring now to FIG. 2, a system 200 for generating cement compositions is illustrated. The system 200 may comprise database 120 as described in FIG. 1 and computer system 210. In some examples, computer system 210 may be the same computer system 115 of FIG. 1. A user input 220 may define engineering parameters such as the required compressive strength of a cement composition, the bottom hole static temperature of the wellbore, the required rheological properties of the slurry, the thickening time of the slurry, available cement materials, available cement additives, available waste materials, free fluid, permeability, pore pressure, fracture gradient, mud weight, density, acid resistance, salt tolerance, and other parameters. Computer system 210 may comprise a predictive cement algorithm and be configured to input user input 220 and the predictive models, reactivity correlations, and data stored in database 120 into the predictive cement algorithm. The predictive cement algorithm may generate a cement composition or compositions that meet the engineering requirements define by the user input 220. The output 230 of the predictive cement algorithm may contain the relative amounts of each cement component in the generated cement composition as well as the predicted material properties of the cement composition. In another example, a user may select a low Portland cement concentration and one or more waste materials as some of the engineering parameters. The meaning of a low Portland cement concentrations was previously discussed. A user may also select a target lime-to-silica ratio, a target lime-to-oxide ratio, or both as part of the engineering parameters. In some examples, the predictive cement algorithm may automatically select a target lime-to-silica ratio and target lime-to-oxide ratio or be configured to select the optimal ratio based on the input from the user. The predictive cement algorithm may generate a cement composition comprising the selected Portland cement concentration and waste materials. In some examples, the predictive cement algorithm may automatically select the waste materials. To select the appropriate ratio of lime to silica, the algorithm may reference the oxide analysis and solubility data mentioned previously. The predictive cement algorithm may be configured to generate the concentrations of cementitious components based on the target lime-to-silica ratio. The predictive cement algorithm may be configured to meet or exceed the target lime-to-silica ratio by adjusting the concentration of one or more cementitious components including lime. For example, the predictive cement algorithm may select to include a concentration of a waste material that has a relatively high in lime and also select a waste material that is relatively high in silica. The predictive cement algorithm may use the target lime-to-silica ratio to balance each of the waste materials comprising lime and silica to meet or exceed the target lime-to-silica ratio.

Although the predictive cement algorithm may generate a cement composition solely based on the lime-to-silica ratio or lime-to-oxide ratio of a user input or automatically chosen value, the algorithm may also generate a cement based on a combination of other factors. One factor may be availability of oxides and lime as a function of time and temperature. As previously described, silicic acid and portlandite may vary in concentration with time and temperature based on the solubility of a cementitious component. As previously described, the available cement components may have differing solubility rates which may also depend on the temperature of solution. A cement component may dissolute relatively slowly at ambient temperature but may dissolute relatively quicker at bottom hole static temperature. As such, the availability of oxides and lime from each component may be dependent not only on time, but also on the position of the cement composition in the wellbore. The predictive cement algorithm may generate a cement composition that maintains the selected lime-to-silica balance throughout the pozzolanic and other cement setting reactions by accounting for the time dependent availability of reactants. As previously mentioned, the varying oxides present in waste materials and other cement components may undergo various reactions to produce a product that is cementitious. Each reaction may have an associated stoichiometry. The predictive cement algorithm may generate a cement composition wherein the stoichiometry of the reactions that may take place is balanced. In some examples, the reactions may be balanced to within plus or minus about 25% of stoichiometric. The predictive cement algorithm may also use cost data from database 120 to generate a cement composition that has the desired lime-to-silica ratio while also reducing the cost of the composition. In some examples the predictive cement algorithm may generate a cement composition with a minimized cost.

Figure 3:
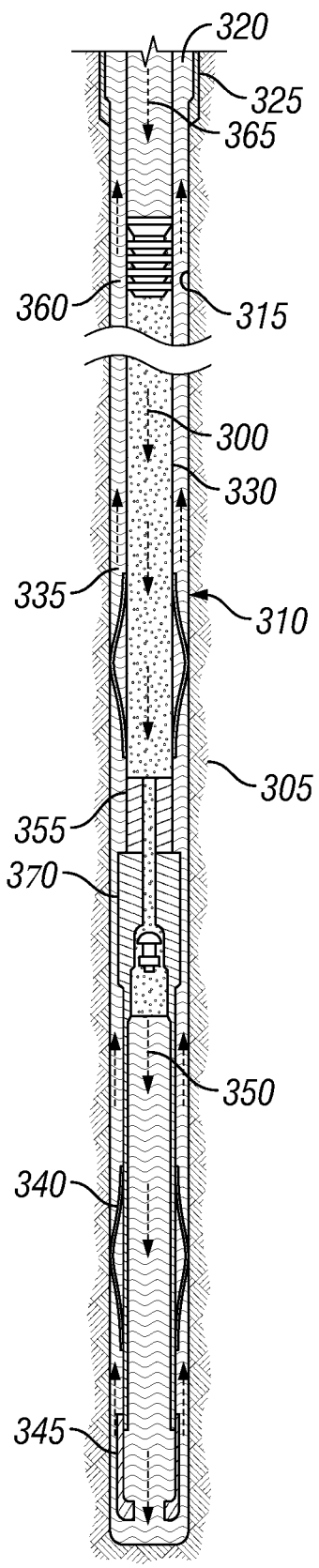
FIG. 3 is a schematic illustration of showing introduction of a cement composition into a wellbore.

Reference is now made to FIG. 3, illustrating use of a cement composition 300 Cement composition 300 may comprise any of the components described herein. Cement composition 300 may be designed, for example, using lime-silica balancing as described herein. Turning now to FIG. 3, the cement composition 300 may be placed into a subterranean formation 305 in accordance with example systems, methods and cement compositions. As illustrated, a wellbore 310 may be drilled into the subterranean formation 305. While wellbore 310 is shown extending generally vertically into the subterranean formation 305, the principles described herein are also applicable to wellbores that extend at an angle through the subterranean formation 305, such as horizontal and slanted wellbores. As illustrated, the wellbore 310 comprises walls 315. In the illustration, a surface casing 320 has been inserted into the wellbore 310. The surface casing 320 may be cemented to the walls 315 of the wellbore 310 by cement sheath 325. In the illustration, one or more additional conduits (e.g., intermediate casing, production casing, liners, etc.), shown here as casing 330 may also be disposed in the wellbore 310. As illustrated, there is a wellbore annulus 335 formed between the casing 330 and the walls 315 of the wellbore 310 and/or the surface casing 320. One or more centralizers 340 may be attached to the casing 330, for example, to centralize the casing 330 in the wellbore 310 prior to and during the cementing operation.

With continued reference to FIG. 3, the cement composition 300 may be pumped down the interior of the casing 330. The cement composition 300 may be allowed to flow down the interior of the casing 330 through the casing shoe 345 at the bottom of the casing 330 and up around the casing 330 into the wellbore annulus 335. The cement composition 300 may be allowed to set in the wellbore annulus 335, for example, to form a cement sheath that supports and positions the casing 330 in the wellbore 310. While not illustrated, other techniques may also be utilized for introduction of the cement composition 300. By way of example, reverse circulation techniques may be used that include introducing the cement composition 300 into the subterranean formation 305 by way of the wellbore annulus 310 instead of through the casing 330. As it is introduced, the cement composition 300 may displace other fluids 350, such as drilling fluids and/or spacer fluids that may be present in the interior of the casing 330 and/or the wellbore annulus 355. While not illustrated, at least a portion of the displaced fluids 350 may exit the wellbore annulus 335 via a flow line and be deposited, for example, in one or more retention pits. A bottom plug 355 may be introduced into the wellbore 310 ahead of the cement composition 300, for example, to separate the cement composition 300 from the fluids 350 that may be inside the casing 330 prior to cementing. After the bottom plug 355 reaches the landing collar 370, a diaphragm or other suitable device may rupture to allow the cement composition 300 through the bottom plug 355. The bottom plug 355 is shown on the landing collar 370. In the illustration, a top plug 360 may be introduced into the wellbore 310 behind the cement composition 300. The top plug 360 may separate the cement composition 300 from a displacement fluid 365 and also push the cement composition 300 through the bottom plug 355.

The disclosed cement compositions and associated methods may directly or indirectly affect any pumping systems, which representatively includes any conduits, pipelines, trucks, tubulars, and/or pipes which may be coupled to the pump and/or any pumping systems and may be used to fluidically convey the cement compositions downhole, any pumps, compressors, or motors (e.g., topside or downhole) used to drive the cement compositions into motion, any valves or related joints used to regulate the pressure or flow rate of the cement compositions, and any sensors (i.e., pressure, temperature, flow rate, etc.), gauges, and/or combinations thereof, and the like. The cement compositions may also directly or indirectly affect any mixing hoppers and retention pits and their assorted variations.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, whenever a numerical range with a lower limit and an upper limit is disclosed, any number and any included range falling within the range are specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values even if not explicitly recited. Thus, every point or individual value may serve as its own lower or upper limit combined with any other point or individual value or any other lower or upper limit, to recite a range not explicitly recited.

Therefore, the present disclosure is well adapted to attain the ends and advantages mentioned as well as those that are inherent therein. The particular examples disclosed above are illustrative only, as the present invention may be modified and practiced in different but equivalent manners apparent to those skilled in the art having the benefit of the teachings herein. Although individual examples are discussed, the invention covers all combinations of all those examples. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative examples disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A method comprising:
    analyzing an industrial byproduct to generate data about physical and/or chemical properties of the industrial byproduct, wherein the data comprises at least silica content, lime content, and water requirement of the industrial byproduct;
    determining a concentration of the byproduct, Portland cement, one or more additional components comprising a silica source and/or lime, and an amount of water based on the data, wherein the amount of water is determined using the water requirement, to provide a settable composition having a silica to lime weight ratio of about 10:1 to about 1:1 and a twenty-four hour destructive compressive strength at 100° F. to 200° F. of about 50 psi or greater; and
    preparing the settable composition comprising the industrial byproduct, Portland cement, water, and the one or more additional components, introducing the settable composition into a subterranean formation, and allowing the settable composition to set.

2. The method of claim 1 wherein the industrial byproduct comprises at least one material selected from the group consisting of fly ash, drill cuttings, cement kiln dust, silica fume, a bio-ash, and combinations thereof.

3. The method of claim 1 wherein the analyzing the industrial byproduct comprises analysis by one or more techniques selected from the group consisting of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio, API testing, and combinations thereof.

4. The method of claim 1 wherein the data comprises an amount of at least one component selected from the group consisting of silica, alumina, iron, calcium, sodium, potassium, magnesium, sulfur, oxides thereof, and combinations thereof.

5. The method of claim 1 wherein the data comprises average particle size, particle size distribution, and morphology.

6. The method of claim 1 wherein the data comprises specific surface area.

7. The method of claim 1 further comprising determining correlations of specific surface to water requirement of the industrial byproduct.

8. The method of claim 1 wherein the settable composition is introduced into the subterranean formation using one or more pumps.

9. The method of claim 1 wherein the preparing the settable composition comprising mixing components of the settable composition using mixing equipment, the components comprising water, the industrial byproduct, and the one or more additional cement components.

10. The method of claim 1 wherein the settable composition further comprises Portland cement.

11. The method of claim 1 further comprising preparing a sample cement composition comprising a cement additive, testing the sample cement composition to determine one or more performance characteristics selected from the group consisting of compressive strength, thickening time, and fluid loss, and adjusting concentration of the cement additive in the sample cement composition in response to the one or more performance characteristics.

12. A system for analyzing industrial byproducts comprising:
    a plurality of industrial byproducts;
    an analytical instrument configured to gather physical and chemical data about the industrial byproducts wherein the data comprises at least silica content, lime content, and water requirement of the industrial byproduct;
    a computer system configured to accept the physical and chemical data and generate determine a concentration of industrial byproduct, Portland cement, water, and the one or more additional components comprising a silica source and/or lime based on the data wherein the concentration of water is determined using the water requirement, to provide a settable composition having a silica to lime weight ratio of about 10:1 to about 1:1 and a twenty-four hour destructive compressive strength at 100° F. to 200° F. of about 50 psi or greater.

13. The system of claim 12 wherein the industrial byproducts comprise at least one material selected from the group consisting of fly ash, drill cuttings, cement kiln dust, silica fume, a bio-ash, and combinations thereof, and wherein each of the industrial byproducts comprise a silica source that is alkali soluble.

14. The system of claim 12 wherein the analytical instrument is configured to perform one or more of the functions selected from the group consisting group consisting of microscopy, spectroscopy, x-ray diffraction, x-ray fluorescence, particle size analysis, water requirement analysis, scanning electron microscopy, energy-dispersive X-ray spectroscopy, surface area, specific gravity analysis, thermogravimetric analysis, morphology analysis, infrared spectroscopy, ultraviolet-visible spectroscopy, mass spectroscopy, secondary ion mass spectrometry, electron energy mass spectrometry, dispersive x-ray spectroscopy, auger electron spectroscopy, inductively coupled plasma analysis, thermal ionization mass spectroscopy, glow discharge mass spectroscopy x-ray photoelectron spectroscopy, mechanical property testing, Young's Modulus testing, rheological properties, Poisson's Ratio, API testing, and combinations thereof.

15. The system of claim 12 wherein the computer system further comprises an algorithm configured to:
   analyze the physical and chemical data and output a predictive model; and
   store the predictive model in a predictive model database.

16. The system of claim 15 wherein the predictive model comprises a correlation of a specific surface area and water requirement of an industrial byproduct.

17. A system for generating cement compositions comprising:
   a predictive model database comprising predictive model data, reactivity maps, and raw data;
   a materials database, wherein the materials database comprise a silica source that is an industrial byproduct and a water requirement of the industrial byproduct;
   a computer system configured to query the databases and accept input from a user; and
   an algorithm capable of generating calculated cement compositions by determining a concentration of industrial byproduct, Portland cement, water, and the one or more additional components comprising a silica source and/or lime based on the data wherein the concentration of water is determined using the water requirement, to provide a settable composition having a silica to lime weight ratio of about 10:1 to about 1:1 and a twenty-four hour destructive compressive strength at 100° F. to 200° F. of about 50 psi or greater.

18. The system of claim 17 wherein the algorithm is configured to generate the calculated cement compositions with a selected industrial byproduct defined by the user, wherein the selected industrial byproduct is the silica source in the materials database.

* * * * *